United States Patent [19]

Doherty et al.

[11] 4,434,175
[45] Feb. 28, 1984

[54] NONSTEROIDAL COMPOUNDS AS ANTI-INFLAMMATORY AND ANALGESIC AGENTS

[75] Inventors: James B. Doherty, New Milford; Michael N. Chang, Westfield; Conrad P. Dorn, Plainfield, all of N.J.

[73] Assignee: Merck & Co., Inc., Rahway, N.J.

[21] Appl. No.: 373,692

[22] Filed: May 3, 1982

Related U.S. Application Data

[63] Continuation-in-part of Ser. No. 291,688, Aug. 10, 1981, abandoned.

[51] Int. Cl.³ .................. A61K 31/405; C07D 207/36
[52] U.S. Cl. .............................. 424/274; 424/248.52; 424/248.55; 424/248.57; 424/250; 424/263; 424/266; 424/267; 544/141; 544/372; 546/208; 546/281; 548/517; 548/518; 548/539
[58] Field of Search ............... 548/539, 518; 544/141, 544/372; 546/208, 281; 424/248.52, 248.55, 248.57, 250, 263, 266, 267, 274, 263, 266

[56] References Cited

U.S. PATENT DOCUMENTS

| | | | |
|---|---|---|---|
| 3,952,012 | 4/1976 | Carson | 548/527 |
| 4,048,191 | 9/1977 | Carson | 424/274 X |
| 4,087,539 | 5/1978 | Muchowski | 424/274 |
| 4,097,579 | 6/1978 | Muchowski | 424/274 |
| 4,119,639 | 10/1978 | Carson | 548/539 |
| 4,232,038 | 11/1980 | Muchowski | 548/562 X |

OTHER PUBLICATIONS

Carson & Wong, *J. Med. Chem.*, 16(2), 172 (1973).

*Primary Examiner*—Richard Raymond
*Attorney, Agent, or Firm*—Theresa Y. Cheng; Mario A. Monaco

[57] ABSTRACT

5-Aroyl-4-RO-, 5-aroyl-4-RS-, 5-aroyl-4-RSO-, 5-aroyl-4-$RSO_2$-, or 5-pyrrylcarbonyl-pyrrole alkanoic acid have been prepared via hydrolysis of a precursor-ester after high temperature decarboxylation or from direct acidic decarboxylation of a precursor diacid. The compounds are analgesic and anti-inflammatory agents of high activities but low ulcerogenic side effects.

12 Claims, No Drawings

NONSTEROIDAL COMPOUNDS AS ANTI-INFLAMMATORY AND ANALGESIC AGENTS

RELATED APPLICATION

This application is a continuation-in-part of application Ser. No. 291,688 filed Aug. 10, 1981, now abandoned.

BACKGROUND OF THE INVENTION

The present invention relates to novel 5-aroyl-4-RO-pyrrole-, 5-aroyl-4-RS-pyrrole-, 5-aroyl-4-RSO-pyrrole-, 5-aroyl-4-$RSO_2$-pyrrole-, or 5-pyrrylcarbonylpyrrole-alkanoic acids and their corresponding salts, esters, nitriles, amides and substituted amides. Unlike the known Zomepirac-related anti-inflammatory agents which are limited to 4-H, 4-alkyl, 4-haloalkyl, or 4-halo derivatives of a 5-aroyl-pyrrole-2-acetic acid, the new compounds of the present invention are substituted with the heteroatoms, oxygen and sulfur. It has been a well-known fact that such hetero-substituted pyrroles are difficult to prepare due to the sensitive nature of the pyrrole system. Furthermore, the compounds of this invention are found to possess anti-inflammatory and analgesic activities comparable to zomepirac and related compounds but exhibit much lower ulcerogenic irritation. For a chronic disease, for example, arthritis, it is crucial that the anti-inflammatory agent be administered routinely and regularly at an effective dosage level without causing gastric irritation or ulcer. Accordingly, it is an object of the present invention
  (1) to provide novel nonsteroidal anti-inflammatory and analgesic agents with high potency but lower ulcerogenic side effect;
  (2) to develop processes for the preparation of the novel 4-RO-, 4-RS-, 4-RSO-, 4-$RSO_2$-, or 5-pyrrylcarbonyl-pyrrole-2-acetic acids;
  (3) to provide methods of application of the novel compounds in the treatment of inflammatory diseases and/or the relief of pain and fever; and
  (4) to provide pharmaceutical compositions and formulations for the administration of these novel compounds.

DETAILED DESCRIPTION OF THE INVENTION

This invention relates to novel 4-RO- or 4-RS-5-aroyl-pyrrole acetic acids and related compounds of the structural formula:

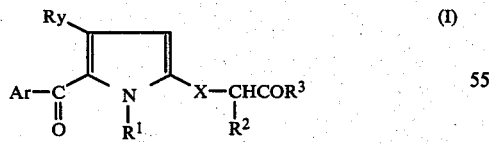

of a pharmaceutically acceptable salt, ester or amide thereof wherein
Ar is
(a) phenyl or lower alkyl-substituted phenyl especially $C_{1-6}$ alkyl-substituted phenyl such as 4-methylphenyl, 4-ethylphenyl, 3-propylphenyl, 2-methylphenyl, 4-(t-butyl)phenyl and 2,4-dimethylphenyl;
(b) halo-loweralkyl-substituted phenyl especially halo $C_{1-3}$ alkyl substituted phenyl such as 4-trifluoromethylphenyl, 4-trichloromethylphenyl, 3-(1',1'-difluoropropyl)phenyl and 2-chloroethylphenyl;
(c) hydroxy- or loweralkoxy-substituted phenyl especially $C_{1-6}$ alkoxy-substituted phenyl such as 4-hydroxyphenyl, 4-methoxyphenyl, 2-ethoxyphenyl, 4-(t-butoxy)phenyl, 1,3-dimethoxyphenyl, and 3,4-methylenedioxyphenyl;
(d) halo-substituted phenyl especially bromo, chloro, or fluoro-substituted phenyl such as 4-chlorophenyl, 4-fluorophenyl, 2-chlorophenyl, 3-fluorophenyl, 4-bromophenyl, 2,4-dichlorophenyl, 4-chloro-2-fluorophenyl, 2,4-difluorophenyl and 3-chlorophenyl;
(e) loweralkylthio-substituted phenyl especially $C_{1-4}$ alkylthio such as 4-methylthiophenyl, 2-ethylthiophenyl and 3-(iso-propyl)thiophenyl;
(f) loweralkylsulfinyl-substituted phenyl especially $C_{1-4}$ alkyl-sulfinylphenyl such as 4-methylsulfinylphenyl, 3-(t-butyl)sulfinylphenyl or 2-(iso-propylsulfinyl)phenyl;
(g) loweralkylsulfonyl-substituted phenyl especially $C_{1-4}$ alkyl-sulfonylphenyl such as 4-methylsulfonylphenyl, 2-(iso-propyl)sulfonylphenyl and 3-(t-butylsulfonyl)phenyl;
(h) pyridyl;
(i) pyrryl or loweralkyl-substituted pyrryl especially $C_{1-6}$ alkyl-substituted pyrryl, for example, 1-methylpyrryl, 3-(isopropyl)pyrryl, 1,3,5-trimethylpyrryl, 5-(t-butyl)pyrryl, 1-methyl-4-ethylpyrryl, 4-cyclopropylpyrryl, and 5-cyclohexylpyrryl;
(j) halo-substituted pyrryl especially bromo, chloro, or fluoro-substituted pyrryl such as 5-chloro-1-methylpyrryl, 4,5-dichloro-1-methylpyrryl, 4-fluoro-pyrryl, 3-fluoro-5-chloropyrryl, and 5-bromo-1-ethylpyrryl;
(k) hydroxy or loweralkoxy-substituted pyrryl especially $C_{1-6}$ alkoxy-substituted pyrryl such as 4-methoxypyrryl, 3,5-dimethoxypyrryl, 4-(t-butoxy)pyrryl, 5-(n-propoxy)-1-methylpyrryl and 3-cyclopentyloxy-1-ethyl-pyrryl;
(l) substituted or unsubstituted pyrryl of formula

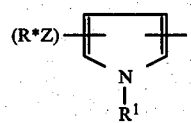

where
(1) n is 0 to 3;
(2) $R^1$ is as defined below;
(3) Z is sulfur, sulfonyl, sulfinyl, or nitrogen; and
(4) R*Z can be at any of the available ring positions and R* is R as defined below;
(m) loweralkenyl-substituted pyrryl especially $C_{2-5}$ alkenyl-substituted pyrryl such as 1-ethenylpyrryl, 2-(1'-propenyl)pyrryl and 3-(3'-cyclohexenyl)pyrryl;
(n) phenyl-substituted pyrryl especially halophenyl-substituted pyrryl such as 1-(2,4-difluorophenyl)pyrryl, 2-(p-chlorophenyl)pyrryl and (2,4-dichlorophenyl)pyrryl;
(o) benzyl-substituted pyrryl such as 1-benzylpyrryl and 1-(p-chlorobenzyl)pyrryl;
(p) furyl; or
(q) thienyl;

R is
(a) hydrogen;
(b) loweralkyl especially $C_{1-6}$ linear or branched alkyl such as methyl, ethyl, propyl, isopropyl, t-butyl, pentyl, and hexyl;
(c) lowercycloalkyl especially $C_{3-6}$ cycloalkyl such as cyclopropyl, cyclobutyl, cyclopentyl and cyclohexyl;
(d) lower(cycloalkyl-alkyl) especially $C_{4-8}$ (cycloalkyl-alkyl) such as cyclopropylmethyl, cyclopentylmethyl, cyclohexylmethyl and cyclohexylethyl;
(e) loweralkenyl especially $C_{2-8}$ alkenyl such as 2-propenyl, 2-methyl-2-butenyl and 3-ethyl-2-pentenyl;
(f) halo-loweralkyl especially halo $C_{1-6}$ alkyl such as chloromethyl, trifluoromethyl, 1-chloroethyl and 2,2-difluorobutyl; or
(g) phenyl- or substituted phenyl-loweralkyl especially phenyl-$C_{1-3}$ alkyl such as benzyl, 4-chlorobenzyl, 2-fluorobenzyl, and phenylpropyl.

Groups (a)–(g) above being unsubstituted or substituted by loweralkyl, loweralkoxy, halo, cyano, carboxy, sulfoamino, carbamoyl, sulfonyl, sulfinyl, azido, amino, substituted amino such as loweralkylamino or diloweralkylamino, haloalkyl, carboxyalkyl, carbamoylalkyl, N-substituted carbamoylalkyl or a combination thereof;

$R^1$ is hydrogen or loweralkyl especially $C_{1-6}$ alkyl as previously defined;

$R^2$ is hydrogen, loweralkyl especially $C_{1-6}$ alkyl as previously defined, or halo especially fluoro, chloro or bromo; and $R^3$ is
(a) hydroxy;
(b) loweralkoxy especially $C_{1-6}$ alkoxy as defined previously;
(c) amino;
(d) loweralkylamino especially $C_{1-6}$ alkylamino such as cyclohexylamino, methylamino, isopropyl amino, n-butylamino or t-butylamino;
(e) diloweralkylamino especially di($C_{1-6}$ alkyl)amino such as diethylamino, or dimethylamino;
(f) morpholinyl;
(g) bis(hydroxyloweralkyl)amino especially bis(hydroxy $C_{1-6}$ alkyl)amino such as bis(hydroxyethyl)amino;
(h) loweralkylcyclohexylamino especially $C_{1-6}$ alkylcyclohexyamino such as methylcyclohexylamino; or
(i) glucosamino;
(j) lower(alkanoyloxyalkoxy), especially $C_{1-6}$ (alkanoyloxyalkoxy) such as 1-(pivaloyloxy)ethoxy or 1-(acetoxy)ethoxy;
(k) aroyloxyloweralkoxy especially 1-(benzoxy)ethoxy;
(l) lower(alkoxycarbonyloxyalkoxy) especially $C_{1-6}$ (alkoxycarbonyloxyalkoxy) such as 1-(ethoxycarbonyloxy)ethoxy;
(m) aryloxycarbonyloxyloweralkoxy especially aryloxycarbonyl $C_{1-6}$ alkoxy such as 1-(benzyloxycarbonyloxy)ethoxy;
(n) tri(loweralkylamino)loweralkoxy especially tri($C_{1-6}$alkylamino) $C_{1-6}$ alkoxy such as cholineoxy;
(o) lower(alkanoylaminoalkoxy), especially $C_{1-6}$ (alkanoylaminoalkoxy) such as acetamidoethoxy;
(p) imidoloweralkoxy especially imido $C_{1-6}$ alkoxy such as 1-(succinimido)ethoxy;
(q) heterocyclyloxy, for example, phthalidyloxy, or 2-pyridyloxy;
(r) hydroxyloweralkoxy especially hydroxy $C_{1-6}$ alkoxy such as hydroxypropoxy;
(s) loweralkoxyalkoxy especially $C_{1-6}$ (alkoxyalkoxy) such as methoxyethoxy, ethoxyethoxy or methoxymethoxy;
(t) di(loweralkylamino)loweralkoxy especially di($C_{1-6}$alkylamino) $C_{1-6}$ alkoxy such as dimethylamino ethoxy, dimethylamino-propoxy, or diethylamino propoxy;
(u) N-pyrrolidinylloweralkoxy especially N-pyrrolidinyl $C_{1-6}$ alkoxy such as N-pyrrolidinylethoxy or N-pyrrolidinyl methoxy and N-methyl-2-pyrrolidinylmethoxy;
(v) N-piperidinylloweralkoxy especially N-piperidinyl $C_{1-6}$ alkoxy such as N-piperidinylethoxy;
(w) N-morpholinylloweralkoxy especially N-morpholinyl $C_{1-6}$alkoxy such as N-morpholinylethoxy; or
(x) 4-methyl-1-piperazinylloweralkoxy especially 4-methyl-1-piperazinyl $C_{1-6}$ alkoxy such as 4-methyl-1-piperazinylethoxy;

X is —(CH$_2$)$_{0-10}$—, —COCH$_2$— or —CH$_2$CO—; and
Y is oxygen, sulfur, sulfinyl, sulfonyl, CH$_2$— or hydrogen providing that when Y is CH$_2$ or hydrogen, Ar can only be substituted or unsubstituted pyrryl; and when Y is hydrogen, R does not exist.

The preferred embodiment of this invention comprises compounds of formula (I) wherein
Ar is
(a) phenyl or 4-methylphenyl;
(b) halo-$C_{1-3}$ alkyl-substituted phenyl such as 4-trifluoromethylphenyl or 3-trichloromethylphenyl;
(c) $C_{1-6}$ alkoxy-substituted phenyl such as 4-methoxyphenyl, 3-propoxyphenyl or 2,4-dimethoxyphenyl;
(d) chloro- or fluoro-substituted phenyl such as 4-fluorophenyl or 2,4-dichlorophenyl or 4-chlorophenyl;
(e) $C_{1-3}$ alkylthio-substituted phenyl such as 4-methylthiophenyl or 2,4-diethylthiophenyl;
(f) $C_{1-3}$ alkylsulfinylphenyl such as 4-methylsulfinylphenyl, or 2,4-diethylsulfinylphenyl;
(g) $C_{1-3}$ alkylsulfonylphenyl such as 4-methylsulfonylphenyl or 2,4-diethylsulfonylphenyl;
(h) 2-pyridyl;
(i) $C_{1-3}$ alkylpyrryl such as 2-(1-methyl)pyrryl, 3-(1-methyl)pyrryl; 2-(1,5-dimethyl)pyrryl, or 2-(1,3,5-trimethyl)pyrryl.
(j) chloro or fluoropyrryl such as 2-(1-methyl-5-chloro)pyrryl, 2-(1-methyl-3-chloro)pyrryl or 2-(1-methyl-4,5-dichloro)pyrryl;
(k) $C_{1-3}$ alkenyl-substituted pyrryl such as 2-(1-allyl)pyrryl; 3-(4-vinyl)pyrryl or
(l) fluoro-phenyl-substituted pyrryl such as 2-[1-(2',4'-difluorophenyl)]pyrryl;
(m)

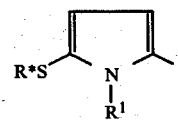

wherein R* and $R^1$ are as defined previously at pages 6-7;

R is
- (a) hydrogen or $C_{1-6}$ alkyl as previously defined;
- (b) $C_{2-4}$ alkenyl such as 2-propenyl or propenylmethyl;
- (c) halo-$C_{1-6}$ alkyl as previously defined; or
- (d) phenyl-$C_{1-3}$ alkyl such as benzyl;

$R^1$ is hydrogen or $C_{1-6}$ alkyl;
$R^2$ is hydrogen, $C_{1-6}$ alkyl, or halo;
$R^3$ is hydroxy or $C_{1-6}$ alkoxy;
X is $(CH_2)_{0-5}$, —$COCH_2$— or $CH_2CO$—; and
Y is oxygen, sulfur, $CH_2$— when Ar is pyrryl, or H when Ar is pyrryl and R is absent.

The most preferred embodiment of this invention comprises compounds of structural formula (I) wherein Ar is
- (a) $C_{1-3}$ haloalkyl-substituted phenyl especially 4-trifluoromethylphenyl;
- (b) methoxy-substituted phenyl;
- (c) 4-chloro- or 4-fluorophenyl;
- (d) methylthiophenyl;
- (e) methylsulfinylphenyl;
- (f) 2,4-dimethylphenyl; or
- (g) loweralkylthio-substituted pyrryl especially $C_{1-6}$ alkylthiopyrryl such as 5-methylthiopyrryl, 3,5-dimethylthiopyrryl, 5-ethylthiopyrryl, 3-(isopropyl)pyrryl, 3-n-hexylthiopyrryl, 5-n-butylthiopyrryl, 4-n-amylthiopyrryl or 4-t-butylthiopyrryl;

R is $C_{1-3}$ alkyl especially methyl;
$R^1$ is hydrogen or methyl;
$R^2$ is hydrogen, methyl or chloro;
$R^3$ is hydroxy, t-butoxy or benzhydryloxy;
X is —$(CH_2)_0$—; and
Y is oxygen, $CH_2$— when Ar is pyrryl, or H when Ar is pyrryl and R is absent.

The representative compounds of this invention comprise

- (a) 4-methoxy-5-(p-chlorobenzoyl)-1-methylpyrrole-2-acetic acid;
- (b) 4-allyloxy-5-(p-chlorobenzoyl)-1-methylpyrrole-2-acetic acid;
- (c) 4-ethoxy-5-(p-chlorobenzoyl)-1-methylpyrrole-2-acetic acid;
- (d) 4-methoxy-5-(p-methylthiobenzoyl)-1-methylpyrrole-2-acetic acid;
- (e) 4-methoxy-5-(p-methylsulfinylbenzoyl)-1-methylpyrrole-2-acetic acid;
- (f) 4-methylthio-5-(p-chlorobenzoyl)-1-methylpyrrole-2-acetic acid;
- (g) 4-methoxy-5-(p-trifluoromethylbenzoyl)-1-methylpyrrole-2-acetic acid;
- (h) 4-methoxy-5-(5-chloro-1-methylpyrrol-2-oyl)-1-methylpyrrole-2-acetic acid;
- (i) 4-methoxy-5-(1-methylpyrryl-2-oyl)-1-methylpyrrole-2-acetic acid;
- (j) 4-methoxy-5-(2-thienyl)carbonyl-1-methylpyrrole-2-acetic acid; or
- (k) 4-methoxy-5-(2'-furyl)carbonyl-1-methylpyrrole-2-acetic acid;
- (l) 1,4-dimethyl-5-(1-methyl-5-chloropyrrol-2-oyl)-pyrrole-2-acetic acid;
- (m) 1,4-dimethyl-5-nicotinoylpyrrole-2-acetic acid;
- (n) 1,4-dimethyl-5-(1-methylpyrrol-2-oyl)pyrrole-2-acetic acid;
- (o) 1,4-dimethyl-5-(1-methyl-5-trifluoromethylpyrrol-2-oyl)pyrrole-2-acetic acid;
- (p) 1,4-dimethyl-5-(1,5-dimethylpyrrol-2-oyl) pyrrole-2-acetic acid; and
- (q) 1,4-dimethyl-5-(1-methyl-5-methylthiopyrrol-2-oyl)pyrrole-2-acetic acid and the acetamidoethyl ester thereof.

The novel compounds of the present invention can be prepared by either of the two precursors IIa or IIb as shown below in schemes (a) and (b):

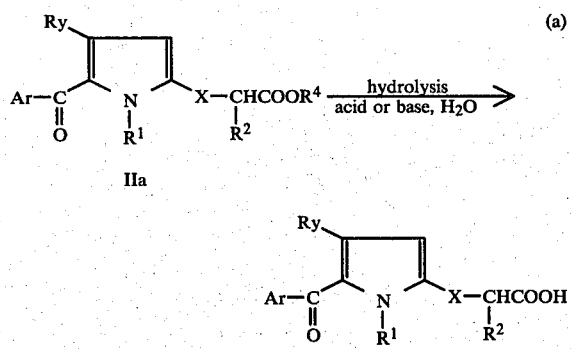

IIa

Wherein Ar, R, Y, $R^1$, $R^2$, and X are as previously defined and $R^4$ is loweralkyl especially $C_{1-6}$ alkyl such as methyl, ethyl, isopropyl, t-butyl, pentyl, or cyclohexyl

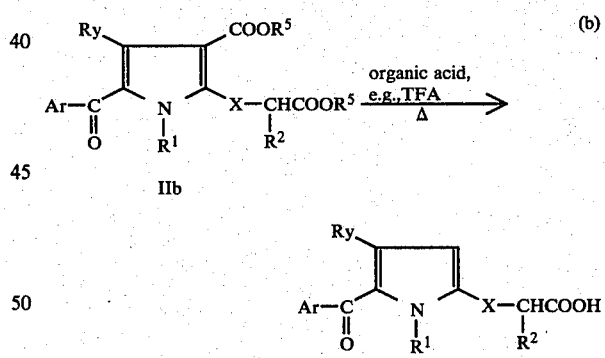

IIb wherein $R^5$ is hydrogen, t-butyl, benzhydryl or other acid-removable protecting groups which can be removed under mild conditions.

According to scheme (a), the ester of formula IIa is usually treated with water in the presence of an acid (table I) or a base (Table II) in an appropriate solvent at about 10°–150° C. preferably about 25°–100° C. for about 0.5–48 hours or until the hydrolysis is substantially complete.

The most commonly utilized solvents comprise
(1) water;
(2) $C_{1-5}$ alkanol especially methanol, ethanol, isopropanol and t-butyl alcohol;
(3) lower ketone, e.g., acetone and methylethylketone;

(4) lower ether including diethylether, 1,2-dimethoxyethane, tetrahydrofuran (THF), dioxane and diglyme;
(5) a liquid acid, e.g., acetic acid and trifluoroacetic acid; or
(6) a mixture of at least two of the solvents described in (1) to (5) especially aqueous solutions thereof.

TABLE I

Common Acids Used in Hydrolysis

Hydrochloric acid or hydrobromic acid
Sulfuric acid
Phosphoric acid
$C_{1-3}$ alkanoic acid e.g. acetic acid
Trifluoroacetic acid
Trichloroacetic acid
p-Toluenesulfonic acid

TABLE II

Common Bases Used in Hydrolysis

Sodium hydroxide
Potassium hydroxide
Sodium or potassium bicarbonate
Sodium or potassium carbonate
Calcium hydroxide
Lithium hydroxide
Tetra(loweralkyl)ammonium hydroxide such tetramethyl or tetraethylammonium hydroxide
Tri-(loweralkyl)amine, e.g., triethylamine
pyridine
collidine According to scheme (b), the precursor of formula IIb is decarboxylated under acidic, mild conditions. For example, 5-(p-chlorobenzoyl)-3-hydroxycarbonyl-4-methoxy-1-methylpyrrole-2-acetic acid or its corresponding di(t-butyl) ester is treated with refluxing trifluoroacetic acid to afford 5-(p-chlorobenzoyl)-4-methoxy-1-methylpyrrole-2-acetic acid. Other acids may also be used. For example, those listed below in Table III.

Table III

Acids Used in the Decarboxylation (1) An acid of the structural formula:

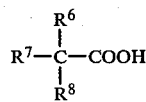

wherein $R^6$ and $R^8$ independently are hydrogen or halo such as iodo, bromo, chloro or fluoro preferably chloro or fluoro; and $R^7$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.

(2) Preferred Acids:
Acetic acid
Chloroacetic acid
Chlorodifluoroacetic acid
Dichloroacetic acid
Difluoroacetic acid
Trifluoroacetic acid
Trichloroacetic acid
Pentafluoropropanoic acid The decarboxylation may be conducted in an acid or in an inert solvent containing the acid. The solvents which are often used are illustrated below in Table IV.

Table IV

Solvents for the Acidic Decarboxylation

Toluene
Benzene
Xylene
Tetrahydrofuran
1,2-Dimethoxy-ethane
Dioxane

The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to about 75° C.

Generally, the decarboxylation is substantially complete after heating at an appropriate temperature for about 1 to about 20 hours or under more favorable conditions, about 0.5 hours to about 5 hours.

The precursors IIa and IIb wherein Y is oxygen are generally prepared, for example, according to the following synthetic scheme:

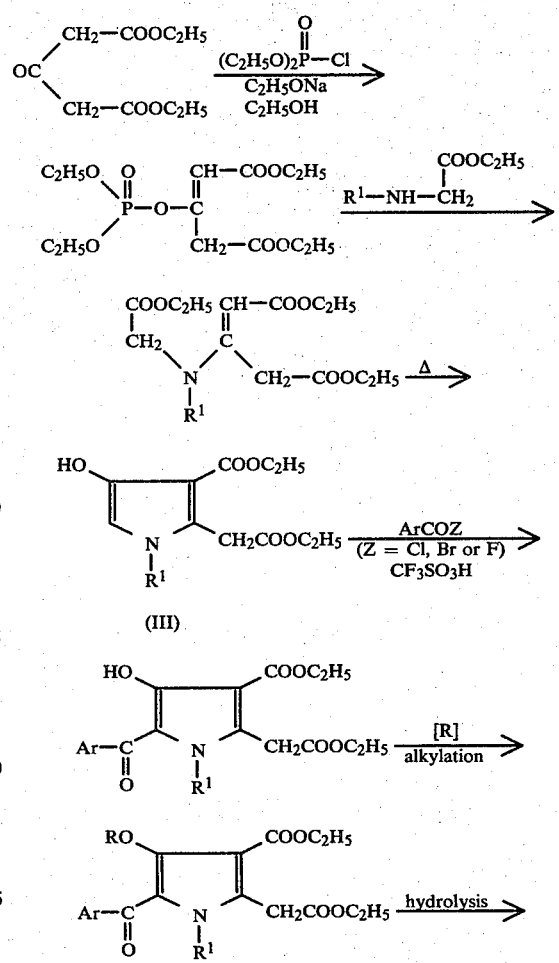

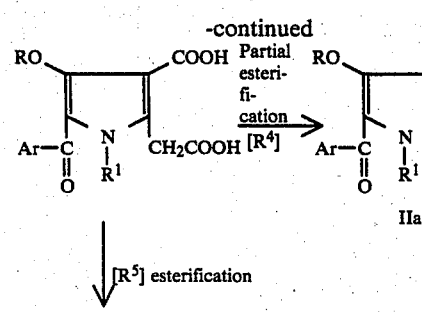
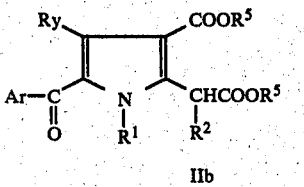
On the other hand, when Y is sulfur, the precursors IIa and IIb are usually prepared via an alternative route, e.g.:
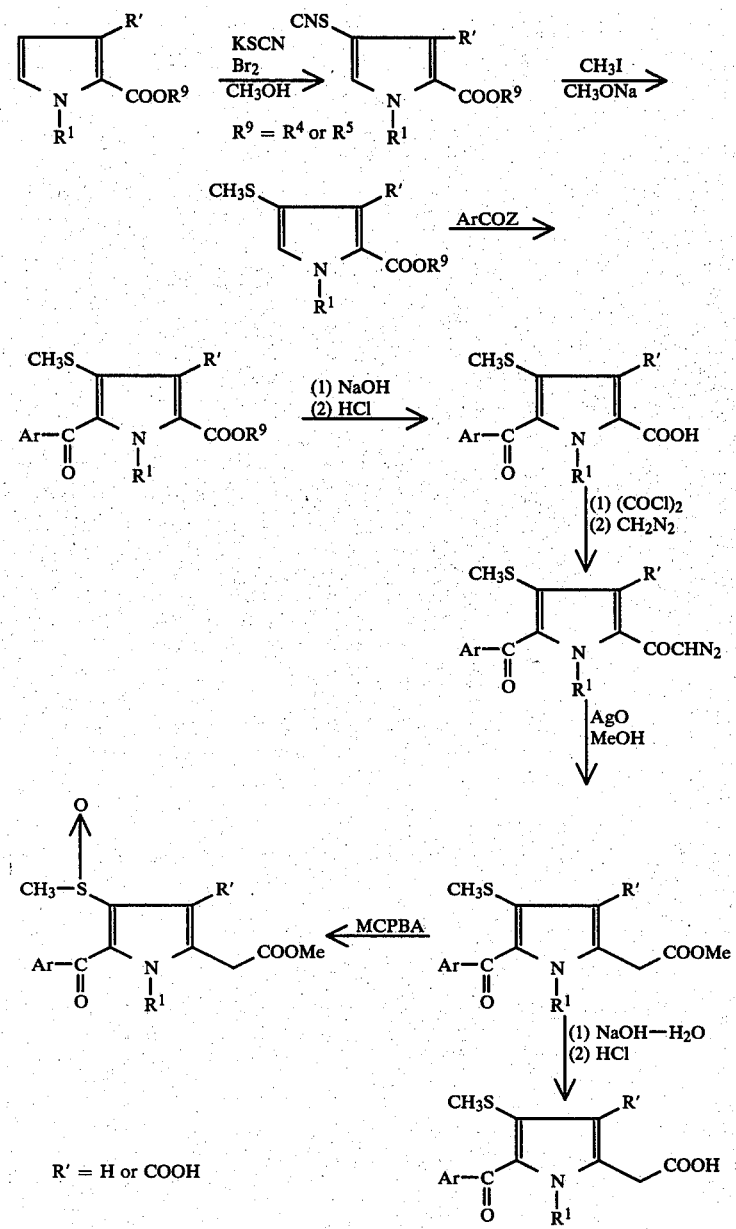
R' = H or COOH
For instance where Ar is a pyrryl or a substituted pyrryl, the following synthetic scheme is applied to obtain the precursor IIa and IIb, e.g.,

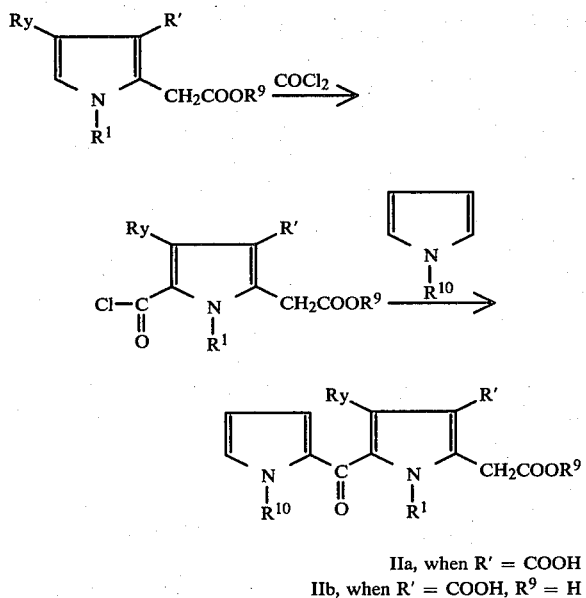

IIa, when R' = COOH
IIb, when R' = COOH, R⁹ = H

Wherein $R^{10}$ is hydrogen lower-alkyl, allyl, halo lower-alkyl, substituted or unsubstituted benzyl or benzoyl.

Alternatively, for example, where Ar is alkylthiopyrryl, the final product may be obtained via the following route:

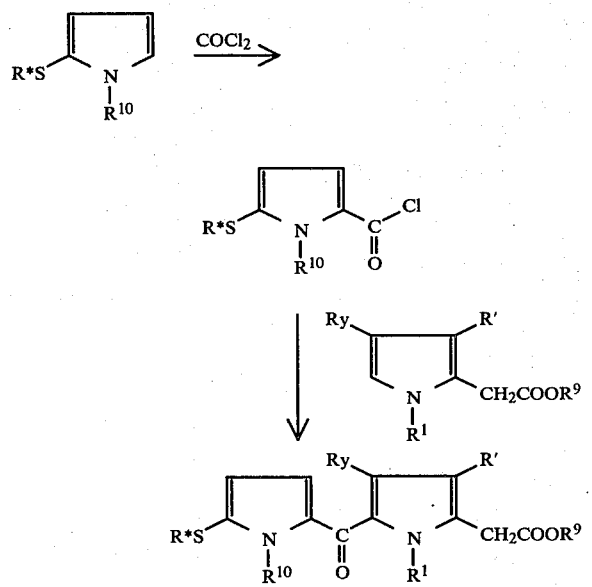

Finally, for the preparation of precursors IIa and IIb wherein Ar is pyridinyl, a unique synthesis employing cyanopyridine as acylation reagent is used, e.g.,

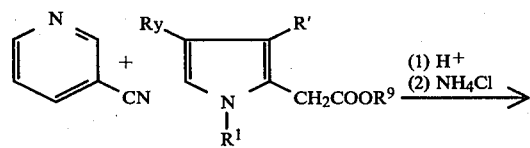

-continued

[structure]

IIa, when R' = COOH
IIb, when R' = COOH;
       R⁹ = H.

The pharmaceutically acceptable salts of the acids of the Formula I are readily prepared by conventional procedures well-known in the art. For example, an acid of Formula I is treated with an appropriate amount of a base, such as an alkali or alkaline earth metal hydroxide, e.g. sodium hydroxide, potassium hydroxide, calcium hydroxide, or an organic base such as an amine, e.g., triethylamine, dibenzylethylenediamine, piperidine, pyrrolidine, benzylamine and the like.

The pharmaceutically acceptable esters of the acids of structural formula (I) are prepared by conventional methods. For example, (1) A compound of Formula (I) is treated with a lower alkanol or phenol in the presence of an acid such as sulfuric acid, hydrochloric acid and any one or a combination of the acids illustrated above in Table (I).

(2) A compound of Formula (I) is converted to an acid halide such as acid chloride or bromide via treatment with a halogenating agent such as thionyl chloride or phosphorus pentachloride, followed by reaction with an alcohol or a phenol. Other well-known methods such as those included in the "Compendium of Organic Synthesis Methods," I. T. Harrison et al., Wiley-Interscience, p. 272 (1971), may also be used.

Similarly, the pharmaceutically acceptable amides of the acids of Formula (I) are readily prepared by conventional methods. For example, the halides of the acids of Formula (I) can be treated with ammonia or substituted amines such as ethylamine, benzylamine or glucosamine to afford the corresponding amides. Other methods involving treatment of the acids with an amine in the presence of a catalyst such as DDC or tosylchloride may also be used.

The following examples are provided for illustrating but not limiting, the scope of the present invention.

EXAMPLE 1

5-(p-chlorobenzoyl)-4-methoxy-1-methylpyrrole-2-acetic acid

Step A: Preparation of Diethyl 3-[N-methyl N-carbethoxymethyl]pent-2-endioate

Diethyl 3-[diethylphosphoryloxy]pent-2-endioate (50.25 g, 0.15 mol) is placed in a one liter flask along with absolute ethanol (275 ml). Sarcosine ethyl ester hydrochloride (34.4 g, 0.225 mol) is added, and the heterogeneous mixture is stirred for five minutes. Triethylamine (27.6 ml, 0.20 mol) is then added over 10 minutes. Solids begin to form soon after addition commences. The mixture is allowed to stir at room temperature for 16 hours. Then the reaction mixture is poured into a four liter separatory funnel containing ether (1500 ml). The organic solution is extracted with water (3×500 ml), brine (200 ml) and dried over sodium sulfate. The solvent is then removed to give 42.4 g of yellow oil. The oil is purified using preparative HPLC (high-pressure liquid chromatography with 3:1/hexane:ethyl acetate as eluent) to give 24.4 g (55%) of diethyl 3-[N-methyl N-carbethoxymethyl]pent-2-endioate.

Anal. calc. for $C_{14}H_{23}NO_6$: C, 55.80; H, 7.69; N, 4.65. Found: C, 56.03; H, 7.84; N, 4.52.

Step B: Preparation of Ethyl 3-ethoxycarbonyl-4-hydroxy-1-methylpyrrole-2-acetate Diethyl 3-[N-methyl-N-carbethoxymethyl]pent-2-endioate (10.0 g, 33.2 mmol) is placed in a 25 ml recovery flask with boiling chips and an alembic stillhead is attached. The flask is evacuated to 100 mm/Hg and the flask is immersed in an oil bath heated to 180°. After a few minutes, ethanol begins to condense in the alembic. Heating is maintained for an additional 15 minutes. The vacuum is then reduced to 0.1 mm/Hg. The ethanol evaporates and a light yellow oil distills into the alembic. When distillation is complete, the system is cooled. The oily product solidifies. The product is transferred to a 25 ml recovery flask (under nitrogen) and recrystallized from ethanol to give 3.57 g of product as a first crop (m.p. 100°–101°). The mother liquor is concentrated to give an additional 2.60 g of material; total yield 6.17 g (73%). The air-sensitive product is stored in the cold under nitrogen.

Step C: Preparation of Ethyl 5-(p-chlorobenzoyl)-3-ethoxycarbonyl-4-hydroxy-1-methylpyrrole-2-acetate Ethyl 3-ethoxycarbonyl-4-hydroxy-1-methylpyrrole-2-acetate (255 mg, 1.0 mmol) is mixed with p-chlorobenzoyl chloride (385 µl, 3.0 mmol) under nitrogen, and 2.0 ml anhydrous trifluoromethanesulfonic acid is added. The reaction mixture is stirred at room temperature for one hour followed by dilution with methylene chloride (50 ml). Solid sodium bicarbonate is slowly added until the acid is neutralized. The solids are filtered off and washed with an additional 50 ml methylene chloride. The combined methylene chloride solutions are washed with water (20 ml) and saturated brine (50 ml). Subsequently, the washed layers are dried with sodium sulfate and the solvent is removed in vacuo to give a red solid which is recrystallized from ethanol to give 275 mg (70%) of ethyl 5-(p-chlorobenzoyl)-3-ethoxycarbonyl-4-hydroxy-1-methylpyrrole-2-acetate, m.p. 145°–147° C.

Following substantially the same procedure as described above in Step C. but substituting for the p-chlorobenzoylchloride used therein benzoyl chloride or any of the various substituted benzoylchlorides as represented below in Table V, there are prepared the corresponding ethyl 5-benzoyl- or 5-substituted-benzoyl-3-ethoxycarbonyl 4-hydroxy-1-methylpyrrole-2-acetate as represented below in Table VI.

Table V (1) benzoyl chloride
(2) p-methylthiobenzoyl chloride
(3) o,p-dichlorobenzoyl chloride
(4) p-methoxybenzoyl chloride
(5) o,p-difluorobenzoyl chloride
(6) p-methylbenzoyl chloride
(7) o,p-dimethylbenzoyl chloride
(8) p-trifluoromethylbenzoyl chloride
(9) p-cyanobenzoyl chloride

Table VI (1) Ethyl 5-benzoyl-3-ethoxycarbonyl 4-methoxy-1-methylpyrrole-2-acetate
(2) Ethyl 5-(p-methylthiobenzoyl)-3-ethoxycarbonyl-4-hydroxy-1-methylpyrrole-2-acetate
(3) Ethyl 5-(o,p-dichlorobenzoyl)-3-ethoxycarbonyl-4-hydroxy-1-methylpyrrole-2-acetate
(4) Ethyl 5-(p-methoxybenzoyl)-3-ethoxycarbonyl-4-hydroxy-1-methylylpyrrole-2-acetate
(5) Ethyl 5-(o,p-difluorobenzoyl)-3-ethoxycarbonyl-4-hydroxy-1-methylpyrrole-2-acetate
(6) Ethyl 5-(p-methylbenzoyl)-3-ethoxycarbonyl-4-hydroxy-1-methylpyrrole-2-acetate
(7) Ethyl 5-(o,p-dimethylbenzoyl)-3-ethoxycarbonyl-4-hydroxy-1-methylpyrrole-2-acetate
(8) Ethyl 5-(p-trifluoromethylbenzoyl)-3-ethoxy-carbonyl-4-hydroxy-1-methylpyrrole-2-acetate
(9) Ethyl 5-(p-cyanobenzoyl)-3-ethoxycarbonyl-4-hydroxy-1-methylpyrrole-2-acetate

Step D: Preparation of Ethyl 5-(p-chlorobenzoyl)-3-ethoxycarbonyl-4-methoxy-1-methylpyrrole-2-acetate Ethyl 5-(p-chlorobenzoyl)-3-ethoxycarbonyl-4-hydroxy-1-methylpyrrole-2-acetate (537 mg, 1.37 mmole) is added to a suspension of 70 mg of 50% sodium hydride (1.46 mmole prewashed with hexanes) in 5 ml of dry dimethylformamide (DMF) under nitrogen. After gas ceased to evolve, 150 µl of dimethylsulfate (1.57 mmole) is added all at once. The resulting yellow-orange solution is stirred for an additional 10 minutes before it is poured into 100 ml of water to precipitate the crude product. The mixture is stirred well followed by filtration. The collected residue is washed with water and dried in vacuo to afford 505 mg of crude ethyl-5-(p-chlorobenzoyl)-3-ethoxycarbonyl-4-methoxy-1-methylpyrrole-2-acetate.

Step E: Preparation of 5-(p-chlorobenzoyl)-3-hydroxycarbonyl-4-methoxy-1-methylpyrrole-2-acetic acid Crude ethyl 5-(p-chlorobenzoyl)-3-ethoxycarbonyl-4-methoxy-1-methylpyrrole-2-acetate (505 mg) is suspended in 1 ml ethanol and heated to reflux. After all the solids dissolve, 5 ml of 2.5 N aqueous sodium hydroxide is added dropwise, causing an oil to separate at the end of the addition. However, the reaction mixture becomes homogeneous again after stirring vigorously at 100° for about 5 min. The reaction is then cooled, diluted with 5 ml water and acidified with 5.5 ml 2.5 N hydrochloric acid. The resulting precipitate is filtered, dried in vacuo to afford 478 mg of crude 5-(p-chlorobenzoyl)-3-hydroxycarbonyl-4-methoxy-1-methylpyrrole-2-acetic acid.

Step F: Preparation of Ethyl 5-(p-chlorobenzoyl)-3-hydroxycarbonyl-4-methoxy-1-methylpyrrole-2-acetate 5-(p-Chlorobenzoyl)-3-hydroxycarbonyl-4-methoxy-1-methylpyrrole-2-acetic acid (478 mg) is suspended in 5 ml of absolute ethanol under nitrogen and heated to reflux. Concentrated hydrochloric acid (75 ml) is subsequently added and the reaction mixture is heated for another 20 minutes until all the solids are dissolved. The resulting solution is heated for an additional 10 minutes. Upon cooling, the product crystallizes out and is filtered, and dried in vacuo to afford 260 mg of ethyl 5-(p-chlorobenzoyl)-3-hydroxycarbonyl-4-methoxy-1-methylpyrrole-2-acetate, m.p. 190 (dec.)

Step G: Preparation of Ethyl 5-(p-chlorobenzoyl)-4-methoxy-1-methylpyrrole-2-acetate To a 10 ml reaction flask with gas inlet tube and outlet tube attached is placed 262 mg (0.684 mmol) ethyl 5-(p-chlorobenzoyl)-3-hydroxycarbonyl-4-methoxy-1-methylpyrrole-2-acetate. The reaction flask is purged 10 times with nitrogen and then heated to 194° under nitrogen. The solid is melted and evolution of gas is observed. After heating for about an hour, the gas evolution stops and the reaction is cooled to room temperature. The resulting glass is dissolved in chloroform and residues removed by filtration. After the solvent is removed by evaporation under reduced pressure, the crude product is used in the next step without further purification.

Step H: Preparation of 5-(p-chlorobenzoyl)-4-methoxy-1-methylpyrrole-2-acetic acid Ethyl-5-(p-chlorobenzoyl)-4-methoxy-1-methylpyrrole-2-acetate (145 mg, 0.475 mmole) is dissolved in 1 ml hot ethanol under nitrogen. Subsequently, 2 ml of 2.5 N aqueous sodium hydroxide is added dropwise. The solution is heated at 95° for about 5 min. The reaction solution is then diluted with water, the product precipitated with 2.5 ml of 2.5 N hydrochloric acid. The resulting precipitate is filtered, washed with water and dried in vacuo to yield 130 mg of 5-(p-chlorobenzoyl)-4-methoxy-1-methylpyrrole-2-acetic acid, m.p. 148 (dec).

Following substantially the same procedures as described in Steps D-H, but substituting for the starting material used in Step D, i.e., ethyl 5-(p-chlorobenzoyl)-3-ethoxycarbonyl-4-hydroxy-1-methylpyrrole-2-acetic acid, the compounds listed in Table VI, there are prepared the following corresponding 5-substituted-4-methoxy-1-methylpyrrole-2-acetic acids:

(1) 5-benzoyl-4-methoxy-1-methylpyrrole-2-acetic acid
(2) 5-(p-methylthiobenzoyl)-4-methoxy-1-methylpyrrole-2-acetic acid
(3) 5-(o,p-dichlorobenzoyl)-4-methoxy-1-methylpyrrole-2-acetic acid
(4) 5-(p-methoxybenzoyl)-4-methoxy-1-methylpyrrole-2-acetic acid
(5) 5-(o-p-difluorobenzoyl)-4-methoxy-1-methylpyrrole-2-acetic acid
(6) 5-(p-methylbenzoyl)-4-methoxy-1-methylpyrrole-2-acetic acid
(7) 5-(o,p-dimethylbenzoyl)-4-methoxy-1-methylpyrrole-2-acetic acid
(8) 5-(p-trifluoromethylbenzoyl)-4-methoxy-1-methylpyrrole-2-acetic acid
(9) 5-(p-cyanobenzoyl)-4-methoxy-1-methylpyrrole-2-acetic acid

EXAMPLE 2

Alternative preparation of 5-(p-chlorobenzoyl)-4-methoxy-1-methylpyrrole-2-acetic acid (from TFA-decarboxylation)

5-(p-Chlorobenzoyl)-3-hydroxycarbonyl-4-methoxy-1-methylpyrrole-2-acetic acid (prepared from Example 1, Step E) is dissolved in 5 ml of trifluoroacetic acid (TFA) and heated to reflux under nitrogen. After about 45 minutes the reaction is substantially complete. It is cooled and concentrated in vacuo. The resultant residue is treated with 10 ml of water, and the precipitate is filtered, and dried to afford 925 mg (81.5%) of 5-(p-chlorobenzoyl)-4-methoxy-1-methylpyrrole-2-acetic acid, m.p. 142°.

EXAMPLE 3

5-(p-Chlorobenzoyl)-4-methylthio-1-methylpyrrole-2-acetic acid

Step A: Preparation of 4-cyanothio-2-methoxycarbonyl-1-methylpyrrole

Potassium thiocyanate (6.44 g, 66 mmol) is suspended in 18 ml of methanol and cooled to −78° under nitrogen. A solution of 1.75 ml of bromine (33 mmol) in 10 ml methanol is added dropwise. The resulting light yellow suspension is stirred for an additional 5 minutes at −78° before 4.17 g (30 mmole) of 2-methoxycarbonyl-1-methylpyrrole in 5 ml methanol is added all at once. After stirring and gradual warming to room temperature, the reaction mixture is poured into 250 ml of ice water, stirred vigorously and filtered. The solid is washed with water, dissolved in methylene chloride, dried over anhydrous sodium sulfate, and concentrated in vacuo to give a white solid which after recrystallization from hexane-ethyl acetate gives 2.8 g of pure 4-cyanothio-2-methoxycarbonyl-1-methylpyrrole.

Step B: Preparation of 2-methoxycarbonyl-4-methylthio-1-methylpyrrole

4-Cyanothio-2-methoxycarbonyl-1-methylpyrrole (2.8 g, 14.3 mmol) is dissolved in 50 ml of methanol under nitrogen. Methyliodide (1.25 ml, 20 mmol) is added followed by 1.08 g (20 mmole) of sodium methoxide. After stirring for about 30 minutes at room temperature, the reaction mixture is concentrated to a paste and then diluted with 100 ml of ethylether. The resulting precipitate is filtered off and the filtrate concentrated to give an oil which is distilled at 100° to 104° at 0.25 mm-Hg to afford 2.2 g (86%) of 2-methoxycarbonyl-4-methylthio-1-methylpyrrole.

Step C: Preparation of 5-(p-chlorobenzoyl)-2-methoxycarbonyl-4-methylthio-1-methylpyrrole p-Chlorobenzoyl chloride (2.75 ml, 20 mmol), dissolved 20 ml of methylene chloride and 2.6 g (20 mmol) of aluminum chloride are mixed well at room temperature. After about 5 minutes 1.87 g (10 mmole) of 2-methoxycarbonyl-4-methylthio-1-methylpyrrole is added dropwise. The reaction mixture turns immediately into a dark red colored solution. The reaction is stirred for one hour before it is diluted with 75 ml of methylene chloride and extracted with water. The methylene chloride layer is separated, washed sucessively with 25 ml sodium bicarbonate solution and 50 ml of saturated brine, dried over anhydrous sodium sulfate and concentrated to an oil. The oil is crystallized from ethanol to give 1.0 g of 5-(p-chlorobenzoyl)-2-methoxycarbonyl-4-methylthio-1-methylpyrrole.

Step D: Preparation of 5-(p-chlorobenzoyl)-2-hydroxycarbonyl-4-methylthio-1-methylpyrrole 5-(p-Chlorobenzoyl)-2-methoxycarbonyl-4-methylthio-1-methylpyrrole (39 mg) is dissolved in 1 ml of warm ethanol and 0.5 ml of 2.5 N sodium hydroxide is added. After standing at room temperature for 30 minutes under nitrogen, 0.7 ml of 2.5 N hydrochloric acid is aded. The resulting precipitate is filtered, washed and dried in vacuo to yield the crude 5-(p-chlorobenzoyl)-2-hydroxycarbonyl-4-methylthio-1-methylpyrrole.

Step E: Preparation of 5-(p-chlorobenzoyl)-2-diazomethylcarbonyl-4-methylthio-1-methylpyrrole To a solution of the crude 5-(p-chlorobenzoyl)-2-hydroxycarbonyl-4-methylthio-1-methylpyrrole in 3 ml of methylene chloride is added 100 μl of (COCl)₂ followed by the addition of 0.5 μl of dimethylformamide (DMF). The resulting reaction mixture is stirred for about an hour and then concentrated to give a yellow solid. Subsequently freshly prepared diazomethane is added dropwise to a stirred solution of the yellow solid in 1 ml of methylene chloride at 0°. The reaction is allowed to warm up to room temperature over a period of one hour. After the excess amount of diazomethane is removed by bubbling nitrogen through the reaction mixture, the solvents are removed by evaporation under reduced pressure and a bright yellow solid is collected. This crude product, i.e., 5-(p-chlorobenzoyl)-2-diazomethylcarbonyl-4-methylthio-1-methylpyrrole, is used directly in the next step without further purification.

Step F: Preparation of methyl 5-(p-chlorobenzoyl)-4-methylthio-1-methylpyrrole-2-acetate A solution of 5-(p-chlorobenzoyl)-2-diazomethylcarbonyl-4-methylthio-1-methylpyrrole (prepared from Step E) in 5 ml of methanol is heated to reflux under nitrogen. Silver oxide (150 mg) is added and the resulting mixture is stirred vigorously and heated for an additional 45 minutes. After cooling and removal of solids by filtration, the filtrate is concentrated to an oil which in turn is purified by preparative TLC to give 19 mg of purified methyl 5-(p-chlorobenzoyl)-4-methylthio-1-methylpyrrole-2-acetate.

Step G: Preparation of 5-(p-chlorobenzoyl)-4-methylthio-1-methylpyrrole-2-acetic acid Methyl-5-(p-chlorobenzoyl)-4-methylthio-1-methylpyrrole-2-acetate (19 mg) is dissolved in 0.5 ml of absolute ethanol. Aqueous sodium hydroxide (1 ml of 2.5 N solution) is added dropwise at a rate such that the reaction stayed homogeneous. Upon completion of the addition, the reaction is allowed to stand for about 30 minutes followed by precipitation with 1.5 ml of 2.5 N aqueous hydrochloride. The resulting precipitate is filtered, and dried in vacuo to afford 15 mg of 5-(p-chlorobenzoyl)-4-methylthio-1-methylpyrrole-2-acetic acid.

Following substantially the same procedure as described in Example 3, Steps C-G, but substituting for 5-(p-chlorobenzoyl) chloride used in Step C the substituted benzoyl chloride listed in Table V, there are prepared the following corresponding analogs of 5-(p-chlorobenzoyl)-4-methylthio-1-methylpyrrole-2-acetic acid:

(1) 5-benzoyl-4-methylthio-1-methylpyrrole-2-acetic acid
(2) 5-(p-methylthiobenzoyl)-4-methylthio-1-methylpyrrole-2-acetic acid
(3) 5-(o,p-dichlorobenzoyl)-4-methylthio-1-methylpyrrole-2-acetic acid
(4) 5-(p-methoxybenzoyl)-4-methylthio-1-methylpyrrole-2-acetic acid
(5) 5-(o,p-difluorobenzoyl)-4-methylthio-1-methylpyrrole-2-acetic acid
(6) 5-(p-methylbenzoyl)-4-methylthio-1-methylpyrrole-2-acetic acid
(7) 5-(o,p-dimethylbenzoyl)-4-methylthio-1-methylpyrrole-2-acetic acid
(8) 5-(p-trifluoromethylbenzoyl)-4-methylthio-1-methylpyrrole-2-acetic acid
(9) 5-(p-cyanobenzoyl)-4-methylthio-1-methylpyrrole-2-acetic acid

EXAMPLE 4

5-(o-Methylbenzoyl)-4-methoxy-1-methylpyrrole-2-acetic acid

Step A. Preparation of ethyl 4-methoxy-3-ethoxycarbonyl-1-methylpyrrole-2-acetate Ethyl 4-hydroxy-3-ethoxycarbonyl-1-methylpyrrole-2-acetate (20 mmole) is dissolved in 10 μl of diethyl ether containing diazomethane freshly prepared from N-methyl-N-nitrosourea and potassium hydroxide. After the reaction is allowed to stand at room temperature for about 0.5 hour, the ether is evaporated under reduced pressure at mild temperature and the residue, i.e., crude ethyl-4-methoxy-3-ethoxycarbonyl-1-methylpyrrole-2-acetate, is used in the next step without further purification.

Step B: Preparation of ethyl 5-(o-methylbenzoyl)-4-methoxy-1-methylpyrrole-2-acetic acid Following substantially the procedures as described in Example 1, Steps C-E, crude ethyl 4-methoxy-3-ethoxycarbonyl-1-methylpyrrole-2-acetate is converted to about 16 mmole of 5-(o-methylbenzoyl)-4-methoxy-3-ethoxycarbonyl-1-methylpyrrole-2-acetate followed by hydrolysis to 5-(o-methylbenzoyl)-4-methoxy-3-hydroxycarbonyl-1-methylpyrrole-2-acetic acid which in turn is decarboxylated in neat TFA according to procedure of Example 2 to afford an overall 50% yield of 5-(o-methylbenzoyl)-4-methoxy-1-methylpyrrole-2-acetic acid.

EXAMPLE 5

1,4-Dimethyl-5-(1-methyl-5-chloropyrrol-2-oyl)pyrrole-2-acetic acid

Step A: Preparation of 1-methyl-2-chloropyrrole

Eight grams (0.1 mole) of 1-methyl pyrrole is dissolved in 100 ml dry ether and stirred at 0° C. when 15 grams (0.11 mole) of sulfuryl chloride in 50 ml ether is added slowly under nitrogen atmosphere. Hydrogen chloride gas evolves and the solution turns yellow immediately. The mixture is stirred at 0° C. for ten minutes and 140 ml of 10% potassium carbonate solution is added and stirred vigorously for 30 minutes. The layers are separated. The ether layer is dried and concentrated to a light yellow liquid. Fractional distillation under reduced pressure (30 mm. 87°-90° C.) yields 7.5 g (65%) of 1-methyl-2-chloropyrrole as a colorless liquid.

Step B: Preparation of ethyl 1,4-dimethyl-5-(1-methyl-5-chloropyrrol-2-oyl)pyrrole-2-acetate 1-Methyl-2-chloropyrrole (5.83 g, 0.05 mole) and ethyl 1,4-dimethyl-5-chlorocarbonylpyrrole-2-acetate (11.5 g, 0.05 mole) are dissolved in 25 ml methylene chloride and stirred under nitrogen atmosphere at 0° C. Thirteen grams (0.05 mole) of $SnCl_4$ in 10 ml methylene chloride is added slowly to the vigorously stirred solution. The resulting orange-brown mixture is stirred at 0° C. for 30 minutes then at room temp. for 3 hours. At the end of this period, 20 ml of 6 N HCl is added and stirred for 30 minutes. The mixture is extracted three times with 100 ml portions of methylene chloride and the crude product is purified by column chromatography and recrystallized from ether/petroleum ether to afford 9.5 g (63% yield) of ethyl 1,4-dimethyl-5-(1-methyl-5'-chloropyrrol-2-oyl)pyrrole-2-acetate.

Step C: Preparation of 1,4-dimethyl-5-(1-methyl-5'-chloropyrrol-2-oyl)pyrrole-2-acetic acid Seven grams of ethyl 1,4-dimethyl-5-(1-methyl-5'-chloropyrrol-2-oyl)pyrrole-2-acetate (0.23 mole) is hydrolyzed with 25 ml 10% NaOH solution at room temperature. After acidifying and extracting with methylene chloride, the crude product is crystallized upon removal of solvent to give 6.1 g (90%) of crystalline 1,4-dimethyl-5-(1-methyl-5'-chloropyrrol-2-oyl)pyrrole-2-acetic acid, m.p. 148°–149° C.

Analysis: Calc'd for $C_{13}H_{15}N_2ClO_3$: C, 57.01; H, 5.12; N, 9.50; Cl, 12.05. Found: C, 56.63; H, 5.34; N, 9.41; Cl, 11.78.

Following substantially the same procedure as described in Example 5, Steps B-C, but substituting for the ethyl 1,4-dimethyl-5-chlorocarbonylpyrrole-2-acetate used in Step B the following analogs thereof:

(1) ethyl 5-chlorocarbonyl-4-methoxy-1-methylpyrrole-2-acetate
(2) ethyl 5-chlorocarbonyl-4-methylthio-1-methyl-1-pyrrole-2-acetate
(3) ethyl 5-chlorocarbonyl-4-methylsulfinyl-1-methylpyrrole-2-acetate.
(4) methyl 5-chlorocarbonyl-4-benzyloxy-1-methylpyrrole-2-acetate
(5) n-propyl 5-chlorocarbonyl-4-benzyloxy-1-methylpyrrole-2-acetate
(6) t-butyl 5-chlorocarbonyl-4-ethoxy-1-allylpyrrole-2-acetate
(7) t-butyl 5-chlorocarbonyl-4-chloro-1-methylpyrrole-2-acetate
(8) ethyl 5-chlorocarbonyl-4-trifluoromethyl-1-methylpyrrole-2-acetate
(9) n-propyl 5-chlorocarbonyl-1,4-dimethylpyrrole-2-(α-methyl)acetate
(10) iso-propyl 5-chlorocarbonyl-1-methylpyrrole-2-(α-methyl)acetate there are prepared the following corresponding derivatives of pyrroyl-2-acetic acids:

(1) 4-methoxy-1-methyl-5-(1-methyl-5-chloropyrrol-2-oyl)pyrrole-2-acetic acid
(2) 1-methyl-5-(1-methyl-5-chloropyrrol-2-oyl)-4-methylthiopyrrole-2-acetic acid
(3) 1-methyl-5-(1-methyl-5-chloropyrrol-2-oyl)-4-methylsulfinylpyrrole-2-acetic acid
(4) 4-allyloxy-1-methyl-5-(1-methyl-5-chloropyrrol-2-oyl)pyrrole-2-acetic acid
(5) 4-benzyloxy-1-methyl-5-(1-methyl-5-chloropyrrol-2-oyl)pyrrole-2-acetic acid
(6) 1-allyl-4-ethoxy-5-(1-methyl-5-chloropyrrol-2-oyl)pyrroyle-2-acetic acid
(7) 4-chloro-1-methyl-5-(1-methyl-5-chloropyrrol-2-oyl)pyrrole-2-acetic acid
(8) 1-methyl-5-(1-methyl-5-chloropyrrol-2-oyl)-4-trifluoromethylpyrrole-2-acetic acid
(9) 1,4-dimethyl-5-(1-methyl-5-chloropyrrol-2-oyl)-pyrrole-2-(α-methyl)acetic acid
(10) 1-methyl-5-(1-methyl-5-chloropyrrol-2-oyl)pyrrole-2-(α-methyl)acetic acid

EXAMPLE 6

1,4-Dimethyl-5-nicotinoylpyrrole-2-acetic acid

Step A: Preparation of ethyl 1,4-dimethyl-3-ethoxycarbonyl-5-nicotinoylpyrrole-2-acetate 3-Cyanopyridine (1.12 g, 0.011 mol) and 2.45 g (0.01 mol) of ethyl 1,4-dimethyl-3-ethoxycarbonylpyrrole-2-acetate are dissolved in 25 ml of dry chloroform and stirred at −10° for 10 minutes. Dry hydrogen chloride gas (HCl) is bubbled into the solution with vigorous stirring. White precipitate is formed initially but gradually redisolved into a pink and then orange solution. Toward the end of the two-hour HCl-bubbling period, the reaction separates into two layers. The top layer is separated and added to 10 ml of water followed by adjustment of pH to 4.0 with aqueous ammonia. The resulting solution is heated to 70° C. for 1.5 hr. before it is extracted 3×100 ml with methylene chloride. The pooled methylene chloride layers are dried over anhydrous sodium sulfate and concentrated in vacuo to afford 2.10 g (60%) of ethyl 1,4-dimethyl-3-ethoxycarbonyl-5-nicotinoylpyrrole-2-acetate.

Step B: Preparation of 1,4-dimethyl-3-hydroxycarbonyl-5-nicotinoylpyrrole-2-acetic acid Two grams of ethyl-1,4-dimethyl-3-ethoxycarbonyl-5-nicotinoylpyrrole-2-acetate (6 mmole) is heated to reflux with 10 ml of 20% aqueous sodium hydroxide solution for two hours. The reaction mixture is cooled to room temp. and acidified to pH 1 with 6 N HCl. The resulting white precipitate is filtered, washed with cold water and dried at room temperature to give crude 1,4-dimethyl-3-hydroxycarbonyl-5-nicotinoylpyrrole-2-acetic acid which is used in the next step without further purification.

Step C: Preparation of 1,4-dimethyl-5-nicotinoylpyrrole-2-acetic acid 1,4-Dimethyl-3-hydroxycarbonyl-5-nicotinoylpyrrole-2-acetic acid (1.5 g) is dissolved in 10 ml of TFA and heated to reflux for 1.5 hr. Upon removal of TFA, the resulting pink solid is dried in vacuo to yield 1.2 g (91% of 1,4-dimethyl-3-hydroxycarbonyl-5-nicotinoylpyrrole-2-acetic acid, m.p. 186°–188° C.

Anal. cald. for $C_{14}H_{17}N_2O_3$: C, 65.1; H, 5.42; N, 10.78. Found: C, 64.4; H, 5.47; N, 10.44.

EXAMPLE 7

1,4-Dimethyl-5-(1-methylpyrrol-2-oyl)pyrrole-2-acetic acid

Step A: Preparation of ethyl 1,4-dimethyl 3-ethoxycarbonyl-5-(1-methylpyrrol-2-oyl)pyrrole-2-acetate Three grams (0.037 mole) of 1-methyl pyrrole and 9 grams of 1,4-dimethyl-5-chlorocarbonyl-3-ethoxycarbonyl pyrrole-2-acetate are dissolved in 50 ml methylene chloride and stirred at 0° C. for 30 minutes followed by additional stirring at room temperature for 3 hours. At the end of this period 20 ml of 6 N HCl is added and the reaction is stirred for 30 minutes. The reaction mixture is extracted three times with 100 ml portions of methylene chloride. After removal of solvent, the crude product is purified by high pressure liquid chromatography (HPLC). A 2:1 ratio of $\alpha:\beta$ isomers are obtained. The yield of the desired $\alpha$-isomer, i.e., ethyl 1,4-dimethyl-3-ethoxycarbonyl-5-(1-methylpyrrol-2-oyl)pyrrole-2-acetate, is 7.2 g (57%).

Step B: Preparation of ethyl 1,4-dimethyl-3-hydroxycarbonyl-5-(1-methylpyrrol-2-oyl)pyrrole-2-acetate Ethyl-1,4-dimethyl-3-ethoxycarbonyl-5-(1-methylpyrrol-2-oyl)pyrrole-2-acetate (7 g) is dissolved in 20 ml of ethanol, aqueous 50% sodium hydroxide solution (50 ml) is added, and the resulting solution is heated at reflux for about one hour. It is cooled to room temperature, and acidified to yield a white precipitate which in turn is filtered and dried to afford 5.2 g of 1,4-dimethyl-3-hydroxycarbonyl-5-(1-methylpyrrol-2-oyl)pyrrole-2-acetic acid (a diacid). The diacid is partially esterified by treatment with 200 ml of ethanol containing 1.0 g of Bio-Rad ® 50W×8 H+ resin at reflux for two hours. After filtration and removal of the excess ethanol, the crude product is purified by HPLC to yield 3.8 g (55%) of white crystalline ethyl 1,4-dimethyl-3-hydroxycarbonyl-5-(1-methylpyrrol-2-oyl)pyrrole-2-acetate.

Step C: Preparation of 1,4-dimethyl-5-(1-methylpyrrol-2-oyl)pyrrole-2-acetic acid Ethyl 1,4-dimethyl-3-hydroxycarbonyl-5-(1-methylpyrrol-2-oyl)pyrrole-2-acetate (3.0 g) is pyrolyzed at 190° under nitrogen for one hour or until carbon dioxide evolution ceases. This reaction mixture is cooled to room temperature followed by treatment with 10 ml of 10% aqueous sodium hydroxide. The resulting mixture is stirred at room temperature for 3 hours before it is converted to 1.7 g of 1,4-dimethyl-5-(1-methylpyrrol-2-oyl)pyrrole-2-acetic acid (m.p. 127°–129°) according to the procedure described in Example 5, Step C.

Anal. Calc. for $C_{13}H_{16}N_2O_3$: C, 64.57; H, 6.19; N, 10.70. Found: C, 64.36; H, 6.33; N, 10.45.

EXAMPLE 8

1,4-Dimethyl-5-(1-methyl-5-trifluoromethylpyrrol-2-oyl)pyrrole-2-acetic acid

Step A: Preparation of ethyl 1,4-dimethyl-3-ethoxycarbonyl-5-(1-methyl-5-trifluoromethylpyrrol-2-oyl)pyrrole-2-acetate A solution of 7.20 g of ethyl 1,4-Dimethyl-3-ethoxycarbonyl-5-(1-methylpyrrol-2-yl)pyrrole-2-acetate (0.02 mole) and 6.5 g of pyridine in 150 ml acetonitrile is chilled to −78° C. when 30 g of trifluoromethyl iodide is added. The mixture is transferred to a quartz vessel containing 10 g of mercury and is photolyzed at room temperature with a Hanovia medium pressure 450 lamp unit. The resulting brown solution is filtered and evaporated to dryness. Column chromatography (silica, 4:1 hexane:ethyl acetate) followed by recrystallization gives 6.1 g (71%) of crystalline ethyl 1,4-dimethyl-3-ethoxycarbonyl-5-(1-methyl-5-trifluoromethylpyrrol-2-oyl)pyrrole-2-acetate.

Step B: Preparation of 1,4-dimethyl-3-hydroxycarbonyl-5-(1-methyl-5p-trifluoromethylpyrrol-2-oyl)pyrrole-2-acetic acid A suspension of 4.30 g (0.01 mole) of ethyl 1,4-dimethyl-3-ethoxycarbonyl-5-(1-methyl-5-trifluoromethylpyrrolyl)pyrrole-2-acetate in 50 ml of a solution of 1:1 ethanol: 20% NaOH in water is heated on a steam bath for three hours. The resulting solution is acidified with 6 N HCl, causing white solid to precipitate. The precipitate is filtered and air dried to recover 2.70 g (73%) of 1,4-dimethyl-3-hydroxycarbonyl-5-(1-methyl-5-trifluoromethylpyrrol-2-oyl)pyrrole-2-acetic acid.

Step C: Preparation of 1,4-dimethyl-5-(1-methyl-5-trifluoromethylpyrroyl)-pyrrole-2-acetic acid A mixture of 1.87 g (5 mmole) of 1,4-dimethyl-3-hydroxycarbonyl-5-(1-methyl-5-trifluoromethylpyrrol-2-oyl)pyrrole-2-acetic acid is heated together with 10 ml trifluoroacetic acid at 80° C. for thirty minutes. TFA is removed in vacuo. The residue is crystallized from ethyl acetate/hexane. After drying, 1.1 g of 1,4-dimethyl-5-(1-methyl-5-trifluoromethylpyrrol-2-oyl)pyrrole-2-acetic acid is obtained.

EXAMPLE 9

1,4-Dimethyl-5-(1,4-dimethylpyrrol-2-oyl)pyrrole-2-acetic acid

Step A: Preparation of 1,2-dimethylpyrrole

1-Methylpyrrole-2-acetic acid (13.9 g, 0.1 mol) was heated to 160° C. under nitrogen. The solid melted while carbon dioxide evolved vigorously. After the carbon dioxide evolution stopped, the resulting red oil was distilled under reduced pressure (30 mm-Hg at 60° C.) to afford 8.5 g (87%) of pure 1,2-dimethylpyrrole.

Step B: Preparation of t-butyl-1,4-dimethyl-5-(1,5-dimethylpyrrol-2-oyl)pyrrole-2-acetate Ten mmole (0.95 g) of 1,2-dimethyl-pyrrole and an equivalent amount of t-butyl 1,4-dimethyl-5-chlorocarbonyl-2-pyrrole acetate were dissolved in 10 ml of methylene chloride and stirred at 0° C. under nitrogen atmosphere. Three grams (12 mmole) of $SnCl_4$ in 10 ml methylene chloride was added dropwise and the resulting mixture was stirred at room temperature for three hours followed by pouring into 25 ml 6 N HCl at 0° C. with vigorous stirring. The resulting suspension was extracted three times with 20 ml portions of methylene chloride. The crude extract was column chromatographed and crystallized from ether/hexane to give 1.6 g (50%) of t-butyl 1,4-dimethyl-5-(1,5-dimethylpyrrol-2-oyl)pyrrole-2-acetate.

Step C: Preparation of 1,4-dimethyl-5-(1,5-dimethylpyrrol-2-oyl)pyrrole-2-acetic acid Following substantially the same procedure as described in Example 5, Step C, or simply by the treatment with trifluoroacetic acid at room temperature, there was obtained 90% yield of 1,4-dimethyl-5-(1,5-dimethylpyrrol-2-oyl)pyrrole-2-acetic acid.

EXAMPLE 10

Acetamidoethyl 1,4-dimethyl-5-(1-methyl-5-methylthiopyrrol-2-oyl)-pyrrole-2-acetate

Step A: Preparation of 1-methyl-5-cyanothiopyrrole

Under nitrogen atmosphere, to a mixture of 25.08 g of KSCN (0.125 mole) in 60 ml dry methanol chilled to −78° C. was added dropwise 20 g of $Br_2$ (in 40 ml methanol). The resulting yellow solution was stirred for 5–10 minutes and 10.1 g (0.125 mole) of the 1-methyl-pyrrole added in one portion. The mixture was allowed to warm to ambient temperature and stirred for one hour. The mixture was poured into 600 ml of ice-water, extracted 2 times with 300 ml $CH_2Cl_2$. The $CH_2Cl_2$ extract was dried and concentrated to 16.1 g (90% yield) of 1-methyl-5-cyanothiopyrrole.

Step B: Preparation of 1-methyl-5-methylthiopyrrole

A mixture of 16.1 g of 1-methyl-2-thiocyanopyrrole and 33 g of methyl iodide was stirred at 0° C. Eleven rams of sodium methoxide was added in one portion. The mixture was stirred at 0° C. for one hour then ambient temperature for three hours. The mixture was concentrated and extracted with ether. After evaporation, there was obtained 14.0 g of 1-methyl-5-methylthiopyrrole.

Step C: Preparation of 1-methyl-5-methylthiopyrrole-2-acid chloride

A solution of 0.1 mole of 1-methyl-2-methylthiopyrrole in 200 ml of dry ether was stirred at 0° C. Eleven grams (0.11 mole) of phosgene dissolved in 20 ml ether was added to this solution. The temperature was maintained at 0°–5° C. for three hours, then room temperature under nitrogen atmosphere for 14 hours. Nitrogen was bubbled through solution to remove residue phosgene. Ether was removed and the residue solid was recrystallized from hexane to afford 17.0 g (90% yield) of crystalline 1-methyl-5-methylthiopyrrole-2-acid chloride.

Step D: Preparation of ethyl-1,4-dimethyl-5-(1-methyl-5-methylthiopyrrol-2-oyl)-3-ethoxycarbonylpyrrole-2-acetate In a 500 ml three neck round bottom flask equipped with a mechanical stirrer and nitrogen inlet, a 250 ml methylene chloride solution of 17.0 g (0.09 mole) 1-methyl-5-methylthiopyrrole acid chloride and 22.7 g of ethyl-1,4-dimethyl-3-ethoxycarbonylpyrrole-2-acetate was stirred at 0° C. Two equivalents of $SnCl_4$ was added slowly with vigorous stirring. The solution turned bright orange then dark orange. It was stirred at 0° C. for two hours then at room temperature for an additional hour. Two hundred ml of 6 N HCl was added and the mixture was stirred for one hour at room temperature. The mixture was extracted 3 times with 200 ml portions of $CH_2Cl_2$. The combined $CH_2Cl_2$ extracts were filtered through 100 g silica gel. Methylene chloride was removed and the light yellow residue was crystallized from ether and hexane to afford a 95% yield of ethyl-1,4-dimethyl-5-(1-methyl-5-methylthiopyrrol-2-oyl)-3-ethoxycarbonylpyrrole-2-acetate.

Step E: Preparation of 1,4-dimethyl-5-(1-methyl-5-methylthiopyrrol-2-oyl)-pyrrole-2-acetic acid Following substantially the same procedures as described in Example 7, steps B, C and D, 10 g of ethyl-1,4-dimethyl-5-(1-methyl-5-methylthiopyrrol-2-oyl)-3-ethoxycarbonylpyrrole-2-acetate was converted in three steps to 6.3 g of 1,4-dimethyl-5-(1-methyl-5-methylthiopyrrol-2-yl)pyrrole-2-acetic acid.

Step F: Preparation of acetamidoethyl-1,4-dimethyl-5-(1-methyl-5-mehylthiopyrrol-2-oyl)pyrrole-2-acetate A mixture of 1.1 g of 1,4-dimethyl-5-(1-methyl-5-methylthiopyrrol-2-oyl)pyrrole-2-acetic acid, 0.52 g of N-acetyl aminoethanol, 1.05 g DCC and 0.21 g of N,N-dimethylaminopyridine in 75 ml dry $CH_2Cl_2$ was stirred at ambient temperature for 16 hours, concentrated and extracted twice with 10 ml portions of $CH_2Cl_2$. The crude product is crystallized from ethyl acetate to yield 0.96 g (70% yield) of acetamidoethyl-1,4-dimethyl-5-(1-methyl-5-methylthiopyrrol-2-oyl)pyrrole-2-acetate.

The novel compounds of this invention are anti-inflammatory, antipyretic, and analgesic agents of value in the treatment of arthritic disorders of like conditions responsive to anti-inflammatory drugs. In general, they are indicated for a wide variety of conditions where one or more of the symptoms of inflammation and pain are manifested, e.g., rheumatoid arthritis, osteoarthritis, gout, infectious arthritis and rheumatic fever. Furthermore, at similar dosage levels, they are found to be as effective as the Zomepirac type compounds known in the art (U.S. Pat. No. 3,952,012), but exhibit a lower incidence of undesirable gastric side effects.

The rat foot edema assay, by which anti-inflammatory activity is determined, is based on the ability of the compounds of Formula I to inhibit the edema induced by injection of an inflammatory (phlogistic) agent into the tissue of a rat's foot. Groups of six male rats (Sprague Dawley strain, 150±30 g each) are given orally the compounds to be tested one hour before 0.1 ml of 1% suspension of carragenin in methocel (0.5%) is injected into the plantar surface of the rat's right hind paw. Immediately and again three hours later, the foot volume is measured and recorded. The difference between the immersion and final volumes is a measurement of the edema produced. For comparative purposes the activity of the compound to be tested is measured against that produced by the known anti-inflammatory agent, e.g. Zomepirac. The activity measured is also corrected by the swelling, if any, produced by the "control" rats which receive only the methocel solution. The results of these tests are as follows:

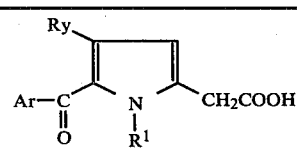

Dose Edema (C.F.E.)

-continued

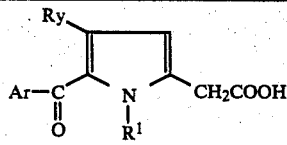

| Ar | RY | R¹ | (mg/kg) | % inhibition |
|---|---|---|---|---|
| 4-Cl—C₆H₅ | CH₃O | CH₃ | 3 | 48 |
| | | | 10 | 51 |
| | | | 20 | 60 |
| | | | 30 | 70 |
| 4-CH₃S—C₆H₅ | CH₃O | CH₃ | 3 | 45 |
| | | | 15 | 64 |
| 4-CH₃SO—C₆H₅ | CH₃O | CH₃ | 10 | 29 |
| | | | 30 | 23 |
| 4-CH₃—C₆H₅ | OCH₃ | CH₃ | 5 | 38 |
| | | | 20 | 38 |
| 4-CF₃—C₆H₅ | OCH₃ | CH₃ | 3 | 24 |
| | | | 10 | 48 |
| | | | 20 | 57 |
| 2,4-F₂—C₆H₅ | OCH₃ | CH₃ | 3 | 29 |
| | | | 10 | 35 |
| | | | 30 | 38 |
| 4-Cl—C₆H₅ | OC₂H₅ | CH₃ | 20 | 33 |
| 4-Cl—C₆H₅ | Cl, O—CH₂C=CH₂ | CH₃ | 3 | 30 |
| | | | 20 | 32 |
| (thiophene) | OCH₃ | CH₃ | 3 | 18 |
| | | | 10 | 21 |
| | | | 30 | 26 |
| (5-Cl-1-methylpyrrol-2-yl) | OCH₃ | CH₃ | 3 | 30 |
| | | | 10 | 35 |
| | | | 30 | 41 |
| (1-methylpyrrol-2-yl) | CH₃ | CH₃ | 30 | 26 |
| (5-Cl-1-methylpyrrol-2-yl) | CH₃ | CH₃ | 10 | 30 |
| | | | 30 | 41 |

-continued

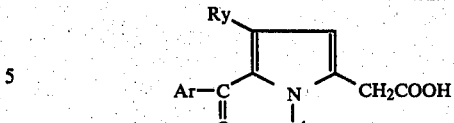

| Ar | RY | R¹ | (mg/kg) | % inhibition |
|---|---|---|---|---|
| (1-methyl-5-methylthiopyrrol-2-yl)** | CH₃ | CH₃ | 10 | 34 |
| | | | 30 | 45 |
| (pyridin-3-yl) | CH₃ | CH₃ | 3 | 34 |
| | | | 10 | 47 |
| | | | 30 | 33 |
| (1-methyl-5-methylthiopyrrol-2-yl) | CH₃ | CH₃ | 10 | 33 |
| | | | 30 | 53 |

**The acetamidoethyl analog of this compound, i.e., acetamido-ethyl-1,4-dimethyl-5-(1-methyl-5-methylthiopyrrol-2-oyl)pyrrole-2-acetate is also active:

| Dose (mg/kg) | Edema (C.F.E.) % inhibition |
|---|---|
| 10 | 13 |
| 30 | 21 |

The active compounds of Formula I and of the compositions of this invention are found to be superior than Zomepirac and related analgesic/anti-inflammatory agents in the Gastric Hemorrhage Lesion Formation Assay (GHLF). In other words, the novel compounds of the present invention are less toxic in terms of gastric irritation. The GHLF test is conducted according to the following procedure:

Rats (Sprague-Dawley, Males, 120–180 gm) were fasted overnight and dosed orally with drug suspended in 0.5% methylcellulose. The drug concentration was adjusted so that each animal received 1.0 ml/100 gm body weight. Four hours later the animals were killed by asphixiation in carbon dioxide, the stomachs removed, cut open and everted. The mucosal lining was washed and examined under 3X magnification. The lesions are indentified as perforations of the gastric mucosa many of which perforate right through the wall of the stomach.

The results are expressed in two ways, the average number of lesions per stomach, and the number of animals in the group showing at least one lesion.

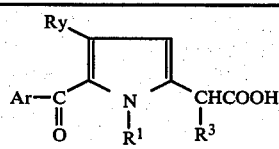

| Ar | Ry | R¹ | R³ | Dose (mg/kg) | No. of Animals Per Group | Ave. lesions per Animal | Animal with Lesion |
|---|---|---|---|---|---|---|---|
| 7-Cl—C₆H₅ (Zomepirac) | CH₃ | CH₃ | H | 3 | 6 | 0.5 | 4/6 |
| | | | | 6 | 6 | 1.4 | 3/6 |
| | | | | 9 | 6 | 1.4 | 6/6 |
| 4-Cl—C₆H₅ | CH₃O | CH₃ | H | 10 | 5 | 0 | 0/5 |
| | | | | 30 | 5 | 0 | 0/5 |
| | | | | 90 | 5 | 2 | 3/5 |
| 4-CH₃S—C₆H₅ | CH₃O— | CH₃— | H | 10 | 6 | 0.5 | 3/6 |

-continued

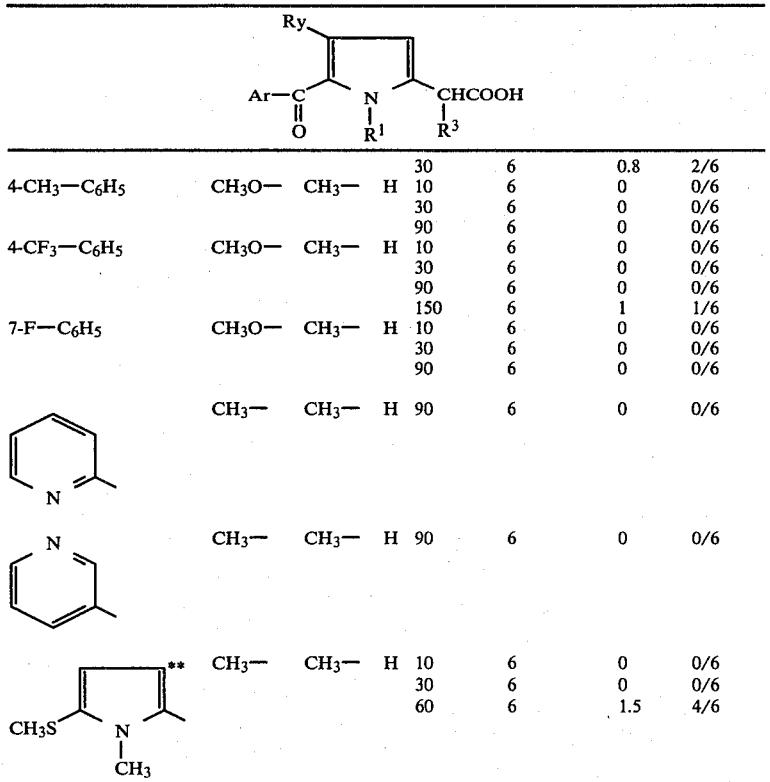

| Ar | Ry | R¹ | R³ | Dose | N | Ave Lesions | Animals w/Lesion |
|---|---|---|---|---|---|---|---|
| | | | | 30 | 6 | 0.8 | 2/6 |
| 4-CH₃—C₆H₅ | CH₃O— | CH₃— | H | 10 | 6 | 0 | 0/6 |
| | | | | 30 | 6 | 0 | 0/6 |
| | | | | 90 | 6 | 0 | 0/6 |
| 4-CF₃—C₆H₅ | CH₃O— | CH₃— | H | 10 | 6 | 0 | 0/6 |
| | | | | 30 | 6 | 0 | 0/6 |
| | | | | 90 | 6 | 0 | 0/6 |
| | | | | 150 | 6 | 1 | 1/6 |
| 7-F—C₆H₅ | CH₃O— | CH₃— | H | 10 | 6 | 0 | 0/6 |
| | | | | 30 | 6 | 0 | 0/6 |
| | | | | 90 | 6 | 0 | 0/6 |
| 2-pyridyl | | CH₃— | CH₃— | H 90 | 6 | 0 | 0/6 |
| 3-pyridyl | | CH₃— | CH₃— | H 90 | 6 | 0 | 0/6 |
| 1-methyl-5-methylthiopyrrol-2-yl ** | | CH₃— | CH₃— | H 10 | 6 | 0 | 0/6 |
| | | | | 30 | 6 | 0 | 0/6 |
| | | | | 60 | 6 | 1.5 | 4/6 |

**The acetamidoethyl analog of this compound, i.e., acetamidoethyl-1,4-dimethyl-5-(1-methylthiopyrrol-2-oyl)pyrrole-2-acetate is also active:

| Dose (mg/kg) | No. of Animals per Group | Ave. Lesions/Animal | Animals with Lesion |
|---|---|---|---|
| 10 | 6 | 0 | 0/6 |
| 30 | 6 | 0 | 0/6 |
| 90 | 6 | 0.5 | 2/6 |

For treatment of inflammation, fever or pain, the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional escipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A compound of the structural formula:

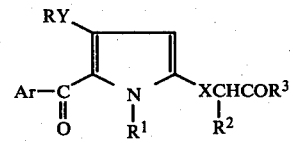

or a pharmaceutically acceptable salt, ester or amide thereof wherein

Ar is
 (a) phenyl or loweralkyl-substituted phenyl;
 (b) halo-loweralkyl-substituted phenyl;
 (c) hydroxy- or loweralkoxy-substituted phenyl;
 (d) halo-substituted phenyl;
 (e) loweralkylthio-substituted phenyl;
 (f) loweralkylsulfinyl-substituted phenyl; or
 (g) loweralkylsulfonyl-substituted phenyl;

R is
 (a) hydrogen;
 (b) loweralkyl;
 (c) lowercycloalkyl;
 (d) lower(cycloalkyl-alkyl);
 (e) loweralkenyl;
 (f) halo-loweralkyl; or
 (g) phenyl- or substituted phenyl-loweralkyl; groups (a)-(g) above being unsustituted or substituted by lower alkyl, lower alkoxy, halo, cyano, carboxy, sulfoamino, carbamoyl, sulfonyl, sulfinyl, azido, amino, substituted amino, haloloweralkyl, carboxyloweralkyl, carbamoylloweralkyl, N-substituted carbamoylloweralkyl or a combination thereof;
R¹ is hydrogen or loweralkyl;
R² is hydrogen, loweralkyl or halo; and
R³ is
  (a) hydroxy;
  (b) loweralkoxy;
  (c) amino;
  (d) loweralkylamino;
  (e) di(loweralkyl)amino;
  (f) morpholinyl;
  (g) bis(hydroxyloweralkyl)amino;
  (h) loweralkylylcyclohexylamino;
  (i) glucosamino;
  (j) lower(alkanoyloxyalkoxy);
  (k) aroyloxyloweralkoxy;
  (l) lower(alkoxycarbonyloxyalkoxy);
  (m) aryloxycarbonyloxyloweralkoxy;
  (n) tri(loweralkylamino)loweralkoxy;
  (o) lower(alkanoylaminoalkoxy);
  (p) hydroxyloweralkoxy;
  (q) loweralkoxyalkoxy;
  (r) di(loweralkylamino)loweralkoxy;
  (s) N-pyrrolidinylloweralkoxy;
  (t) N-piperidinylloweralkoxy;
  (u) N-morpholinylloweralkoxy; or
  (v) 4-methyl-1-piperazinylloweralkoxy.
X is —(CH₂)₀₋₁₀—, —COCH₂— or —CH₂CO—; and
Y is oxygen, sulfur, sulfinyl, or sulfonyl.

2. The compound of claim 1 wherein
Ar is
  (a) phenyl or 4-methylphenyl;
  (b) halo-C₁₋₃ alkyl-substituted phenyl;
  (c) C₁₋₆ alkoxy-substituted phenyl;
  (d) chloro- or fluoro-substituted phenyl;
  (e) C₁₋₃ alkylthio-substituted phenyl;
  (f) C₁₋₃ alkylsulfinylphenyl; or
  (g) C₁₋₃ alkylsulfonylphenyl;
R is
  (a) H or C₁₋₆ alkyl;
  (b) C₂₋₄ alkenyl;
  (c) halo-C₁₋₆ alkyl; or
  (d) phenyl-C₁₋₃ alkyl.
R¹ is hydrogen or C₁₋₆ alkyl;
R² is hydrogen or C₁₋₆ alkyl;
R³ is hydroxy or C₁₋₆ alkoxy;
X is (CH₂)₀₋₅, —COCH₂— or CH₂CO—; and
Y is oxygen or sulfur.

3. The compound of claim 1 wherein
Ar is
  (a) C₁₋₃ haloalkyl-substituted phenyl;
  (b) methoxy-substituted phenyl;
  (c) 4-chloro-or 4-fluorophenyl;
  (d) methylthiophenyl;
  (e) methylsulfinylphenyl; or
  (f) 1,4-dimethylphenyl;
R is C₁₋₃ alkyl;
R¹ is hydrogen or methyl;
R² is hydrogen, methyl or chloro;
R³ is hydroxy or t-butoxy;
X is —(CH₂)₀; and
Y is oxygen.

4. The compound of claim 1 which is
  (a) 4-methoxy-5-(p-chlorobenzoyl)-1-methylpyrrole-2-acetic acid;
  (b) 4-allyloxy-5-(p-chlorobenzoyl)-1-methylpyrrole-2-acetic acid;
  (c) 4-ethoxy-5-(p-chlorobenzoyl)-1-methylpyrrole-2-acetic acid;
  (d) 4-methoxy-5-(p-methylthiobenzoyl)-1-methylpyrrole-2-acetic acid;
  (e) 4-methoxy-5-(p-methylsulfinylbenzoyl)-1-methylpyrrole-2-acetic acid;
  (f) 4-methylthio-5-(p-chlorobenzoyl)-1-methylpyrrole-2-acetic acid; or
  (g) 4-methoxy-5-(p-trifluoromethylbenzoyl)-1-methylpyrrole-2-acetic acid;

5. A pharmaceutical composition for treating inflammatory conditions, fever and pain in mammalian species comprising a non-toxic pharmaceutical carrier and an effective amount of a compound of structural formula:

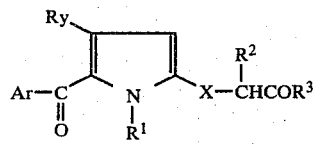

or a pharmaceutically acceptable salt, ester or amide thereof wherein
Ar is
  (a) phenyl or loweralkyl-substituted phenyl;
  (b) halo-loweralkyl-substituted phenyl;
  (c) hydroxy- or loweralkoxy-substituted phenyl;
  (d) halo-substituted phenyl;
  (e) loweralkylthio-substituted phenyl;
  (f) loweralkylsulfinyl-substituted phenyl;
  (g) loweralkylsulfonyl-substituted phenyl;
R is
  (a) hydrogen;
  (b) loweralkyl;
  (c) lowercycloalkyl;
  (d) lower(cycloalkyl-alkyl);
  (e) loweralkenyl;
  (f) halo-loweralkyl; or
  (g) phenyl- or substituted phenyl-loweralkyl; groups (a)-(g) above being unsustituted or substituted by lower alkyl, lower alkoxy, halo, cyano, carboxy, sulfoamino, carbamoyl, sulfonyl, sulfinyl, azido, amino, substituted amino, haloloweralkyl, carboxyloweralkyl, carbamoylloweralkyl, N-substituted carbamoylloweralkyl or a combination thereof;
R¹ is hydrogen or loweralkyl;
R² is hydrogen, loweralkyl or halo; and
R³ is
  (a) hydroxy;
  (b) loweralkoxy;
  (c) amino;
  (d) loweralkylamino;
  (e) di(loweralkyl)amino;
  (f) morpholinyl;
  (g) bis(hydroxyloweralkyl)amino;
  (h) loweralkylcyclohexylamino;
  (i) glucosamino;
  (j) lower(alkanoyloxyalkoxy);
  (k) aroyloxyloweralkoxy;
  (l) lower(alkoxycarbonyloxyalkoxy);
  (m) aryloxycarbonyloxyloweralkoxy;
  (n) tri(loweralkylamino)loweralkoxy;
  (o) lower(alkanoylaminoalkoxy);
  (p) hydroxyloweralkoxy;

(q) loweralkoxyalkoxy;
(r) di(loweralkylamino)loweralkoxy;
(s) N-pyrrolidinylloweralkoxy;
(t) N-piperidinylloweralkoxy;
(u) N-morpholinylloweralkoxy; or
(v) 4-methyl-1-piperazinylloweralkoxy.

X is $-(CH_2)_{0-10}-$, $-COCH_2-$ or $-CH_2CO-$; and
Y is oxygen, sulfur, sulfinyl, or sulfonyl.

6. The pharmaceutical composition of claim 5 wherein
Ar is
  (a) phenyl or 4-methylphenyl;
  (b) halo-$C_{1-3}$ alkyl-substituted phenyl;
  (c) $C_{1-6}$ alkoxy-substituted phenyl;
  (d) chloro- or fluoro-substituted phenyl;
  (e) $C_{1-3}$ alkylthio-substituted phenyl;
  (f) $C_{1-3}$ alkylsulfinylphenyl; or
  (g) $C_{1-3}$ alkylsulfonylphenyl;
R is
  (a) H or $C_{1-6}$ alkyl;
  (b) $C_{2-4}$ alkenyl;
  (c) halo-$C_{1-6}$ alkyl; or
  (d) phenyl-$C_{1-3}$ alkyl.
$R^1$ is hydrogen or $C_{1-6}$ alkyl;
$R^2$ is hydrogen or $C_{1-6}$ alkyl;
$R^3$ is hydroxy or $C_{1-6}$ alkoxy;
X is $(CH_2)_{0-5}$, $-COCH_2-$ or $CH_2CO$; and
Y is oxygen or sulfur.

7. The pharmaceutical composition of claim 5 wherein
Ar is
  (a) $C_{1-3}$ haloalkyl-substituted phenyl;
  (b) methoxy-substituted phenyl;
  (c) 4-chloro-or 4-fluorophenyl;
  (d) methylthiophenyl;
  (e) methylsulfinylphenyl; or
  (f) 1,4-dimethylphenyl;
R is $C_{1-3}$ alkyl;
$R^1$ is hydrogen or methyl;
$R^2$ is hydrogen, methyl or chloro;
$R^3$ is hydroxy or t-butoxy;
X is $-(CH_2)_0$; and
Y is oxygen.

8. The pharmaceutical composition of claim 5 wherein
(a) 4-methoxy-5-(p-chlorobenzoyl)-1-methylpyrrole-2-acetic acid;
(b) 4-allyloxy-5-(p-chlorobenzoyl)-1-methylpyrrole-2-acetic acid;
(c) 4-ethoxy-5-(p-chlorobenzoyl)-1-methylpyrrole-2-acetic acid;
(d) 4-methoxy-5-(p-methylthiobenzoyl)-1-methylpyrrole-2-acetic acid;
(e) 4-methoxy-5-(p-methylsulfinylbenzoyl)-1-methylpyrrole-2-acetic acid;
(f) 4-methylthio-5-(p-chlorobenzoyl)-1-methylpyrrole-2-acetic acid; or
(g) 4-methoxy-5-(p-trifluoromethylbenzoyl)-1-methylpyrrole-2-acetic acid;

9. A method of treatment of inflammatory conditions, fever and pain which comprises the administration to a mammalian species in need of such treatment an effective amount of a compound of structural formula (I)

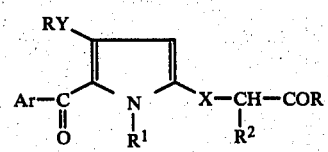

or a pharmaceutically acceptable salt, ester or amide thereof wherein
Ar is
  (a) phenyl or loweralkyl-substituted phenyl;
  (b) halo-loweralkyl-substituted phenyl;
  (c) hydroxy- or loweralkoxy-substituted phenyl;
  (d) halo-substituted phenyl;
  (e) loweralkylthio-substituted phenyl;
  (f) loweralkylsulfinyl-substituted phenyl;
  (g) loweralkylsulfonyl-substituted phenyl;
R is
  (a) hydrogen;
  (b) loweralkyl;
  (c) lowercycloalkyl;
  (d) lower(cycloalkyl-alkyl);
  (e) loweralkenyl;
  (f) halo-loweralkyl; or
  (g) phenyl- or substituted phenyl-loweralkyl; groups (a)-(g) above being unsubstituted or substituted by lower alkyl, lower alkoxy, halo, cyano, carboxy, sulfoamino, carbamoyl, sulfonyl, sulfinyl, azido, amino, substituted amino, halo-loweralkyl, carboxyloweralkyl, carbamoylloweralkyl, N-substituted carbamoylloweralkyl or a combination thereof;
$R^1$ is hydrogen or loweralkyl;
$R^2$ is hydrogen, loweralkyl or halo; and
$R^3$ is
  (a) hydroxy;
  (b) loweralkoxy;
  (c) amino;
  (d) loweralkylamino;
  (e) di(loweralkyl)amino;
  (f) morpholinyl;
  (g) bis(hydroxyloweralkyl)amino;
  (h) loweralkylcyclohexylamino;
  (i) glucosamino;
  (j) lower(alkanoyloxyalkoxy);
  (k) aroyloxyloweralkoxy;
  (l) lower(alkoxycarbonyloxyalkoxy);
  (m) aryloxycarbonyloxyloweralkoxy;
  (n) tri(loweralkylamino)loweralkoxy; or
  (o) lower(alkanoylaminoalkoxy);
  (p) hydroxyloweralkoxy;
  (q) loweralkoxyalkoxy;
  (r) di(loweralkylamino)loweralkoxy;
  (s) N-pyrrolidinylloweralkoxy;
  (t) N-piperidinylloweralkoxy;
  (u) N-morpholinylloweralkoxy; or
  (v) 4-methyl-1-piperazinylloweralkoxy.

X is $-(CH_2)_{0-10}-$, $-COCH_2-$ or $-CH_2CO-$; and
Y is oxygen, sulfur, sulfinyl, or sulfonyl.

10. The method of claim 9 wherein
Ar is
  (a) phenyl or 4-methylphenyl;
  (b) halo-$C_{1-3}$ alkyl-substituted phenyl;
  (c) $C_{1-6}$ alkoxy-substituted phenyl;
  (d) chloro- or fluoro-substituted phenyl;
  (e) $C_{1-3}$ alkylthio-substituted phenyl;
  (f) $C_{1-3}$ alkylsulfinylphenyl;

(g) $C_{1-3}$ alkylsulfonylphenyl;

R is
(a) H or $C_{1-6}$ alkyl;
(b) $C_{2-4}$ alkenyl;
(c) halo-$C_{1-6}$ alkyl; or
(d) phenyl-$C_{1-3}$ alkyl.

$R^1$ is hydrogen or $C_{1-6}$ alkyl;
$R^2$ is hydrogen or $C_{1-6}$ alkyl;
$R^3$ is hydroxy or $C_{1-6}$ alkoxy;
X is $(CH_2)_{0-5}$, —$COCH_2$— or $CH_2CO$—; and
Y is oxygen or sulfur.

11. The method of claim 9 wherein
Ar is
(a) $C_{1-3}$ haloalkyl-substituted phenyl;
(b) methoxy-substituted phenyl;
(c) 4-chloro- or 4-fluorophenyl;
(d) methylthiophenyl;
(e) methylsulfinylphenyl; or
(f) 1,4-dimethylphenyl;

R is $C_{1-3}$ alkyl;
$R^1$ is hydrogen or methyl;
$R^2$ is hydrogen, methyl or chloro;
$R^3$ is hydroxy or t-butoxy;
X is —$(CH_2)_0$; and
Y is oxygen.

12. The method of claim 9 wherein the compound
(a) 4-methoxy-5-(p-chlorobenzoyl)-1-methylpyrrole-2-acetic acid;
(b) 4-allyloxy-5-(p-chlorobenzoyl)-1-methylpyrrole-2-acetic acid;
(c) 4-ethoxy-5-(p-chlorobenzoyl)-1-methylpyrrole-2-acetic acid;
(d) 4-methoxy-5-(p-methylthiobenzoyl)-1-
(e) 4-methoxy-5-(p-methylsulfinylbenzoyl)-1-methylpyrrole-2-acetic acid;
(f) 4-methylthio-5-(p-chlorobenzoyl)-1-methylpyrrole-2-acetic acid; or
(g) 4-methoxy-5-(p-trifluoromethylbenzoyl)-1-methylpyrrole-2-acetic acid.

* * * * *

UNITED STATES PATENT AND TRADEMARK OFFICE
CERTIFICATE OF CORRECTION

PATENT NO. : 4,434,175

DATED : February 28, 1984

INVENTOR(S) : Doherty et al.

It is certified that error appears in the above—identified patent and that said Letters Patent is hereby corrected as shown below:

Column 33, line 49, after "wherein" in Claim 8, insert -- the compound is --.

Column 36, line 13, after "(d) 4-methoxy-5-(p-methylthiobenzoyl)-1-" insert -- methyl-pyrrole-2-acetic acid; --.

Signed and Sealed this

Thirtieth Day of October 1984

[SEAL]

Attest:

Attesting Officer

GERALD J. MOSSINGHOFF

Commissioner of Patents and Trademarks